United States Patent [19]

Kampe

[11] Patent Number: 5,554,751

[45] Date of Patent: Sep. 10, 1996

[54] AMINOUREIDOFULLERENE AND AMINOTHIOUREIDOFULLERENE DERIVATIVES AND PROCESS FOR THE PREPARATION THEREOF

[75] Inventor: Klaus-Dieter Kampe, Bad Soden, Germany

[73] Assignee: Hoechst Aktiengesellschaft, Germany

[21] Appl. No.: 337,937

[22] Filed: Nov. 10, 1994

[30] Foreign Application Priority Data

Nov. 12, 1993 [DE] Germany ............ 43 38 672.5

[51] Int. Cl.$^6$ ............ C07D 225/08; C07D 223/14; C07D 221/18

[52] U.S. Cl. ............ 544/338; 544/229; 540/471; 540/555

[58] Field of Search ............ 544/338, 229; 540/471, 555

[56] References Cited

FOREIGN PATENT DOCUMENTS

WO94/05671  3/1994  WIPO .

OTHER PUBLICATIONS

Angewandt Chemie, Aug. 1993, pp. 1138–1141 entitled "The Chemistry of the Fullerener: An Overview", by Andreas Hirsch. Month of publication not provided.

Angewandt Chemie, Aug. 1993, p. 1175 entitled "Diamino and Tetraamino Derivatives of Buckminsterfullerene $C_{60}$", by Kampe et al. Month of publication not provided.

Angewandt Chemie, 1992, pp. 808–810 entitled "Titration von $C_{60}$: eine Methode zur Synthese von Organofullerene." Month of publication not provided.

Angew Chemical Int. Edition, 1992, No. 6, by Hirsch et al., entitled "Titration of $C_{60}$: A Method for the Synthesis of Organofullerenes", pp. 766–768. Publication month not provided.

American Chemical Society, 1992, by Wudl et al., entitled "Survey of Chemical Reactivity of $C_{60}$, Electrophile and Dieno–polarophile Par Excellence," pp. 161–175. Publication month not provided.

Angew Chemical Int. Edition, 1993, No. 8, by Klaus–Dieter Kampe et al. entitled "Diamino and Tetraamino Derivatives of Buckminsterfullerence $C_{60}$", pp. 1174–1176. Publication month not provided.

*Primary Examiner*—Mukund J. Shah
*Assistant Examiner*—King Lit Wong
*Attorney, Agent, or Firm*—Curtis, Morris & Safford P C

[57] ABSTRACT

Aminoureidofullerene and aminothioureidofullerene derivatives and the process for the preparation thereof Aminoureido and aminothioureido compounds of the fullerenes $C_{60}$ and/or $C_{70}$ and processes for the preparation thereof and use thereof are described.

5 Claims, No Drawings

AMINOUREIDOFULLERENE AND AMINOTHIOUREIDOFULLERENE DERIVATIVES AND PROCESS FOR THE PREPARATION THEREOF

The invention relates to new aminoureido and aminothioureido compounds of the fullerenes $C_{60}$ and/or $C_{70}$ and processes for the preparation thereof and use thereof.

Chemical reactions with the fullerenes $C_{60}$ and/or $C_{70}$ are possible in principle, but frequently proceed, since $C_{60}$ and $C_{70}$ are polyfunctional molecules, with formation of complex mixtures of reaction products which cannot be separated. This applies both to the number of reactions which have occurred or radicals which have been introduced on $C_{60}$ and/or $C_{70}$ and to the different relative structures of possible regioisomers [A. Hirsch, A. Soi., H. R. Karfunkel, Angew. Chemie 1992, 104, 808; F. Wudl, A. Hirsch, K. C. Khemani, T. Suzuki, P.-M. Allemand, A. Koch, H. Eckert, G. Srdanov, H. Webb, in Fullerenes: Synthesis, Properties and Chemistry of Large Carbon Clusters; Hammond, G. S.; Kuck, V. S., Eds.; Washington, DC, 1992; p. 161].

German Patent Application P 43 12 632.4 describes readily obtainable, defined, diamino derivatives of the fullerenes $C_{60}$ and $C_{70}$ which can be isolated in pure form and which contain, besides a tertiary amino group, an NH function.

Subsequent reactions with fullerene derivatives are very frequently made difficult or fail completely because of the sparing solubility or insolubility of the starting fullerene derivatives in the inert solvents which can be used therefor. Reactions with $C_{60}$ and/or $C_{70}$ derivatives also often proceed very sluggishly and require relatively high reaction temperatures and long reaction times which frequently cannot be used because of the insufficient stability of the fullerene starting materials and/or the fullerene products to be prepared.

Owing to the defined and characterized synthetic fullerene compounds which are often obtainable only by a very complicated procedure, targeted subsequent reactions on functional fullerene derivatives have hitherto been successfully carried out only in few cases.

It is therefore an object of the invention to provide readily obtainable, defined aminoureido and aminothioureido compounds which can be isolated in pure form.

The invention provides aminoureido- or aminothioureido-$C_{60}$ and/or $C_{70}$ compounds of the formula I

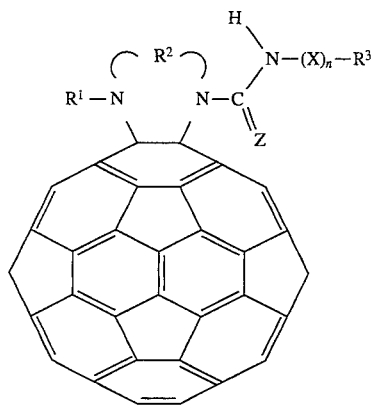

and/or II,

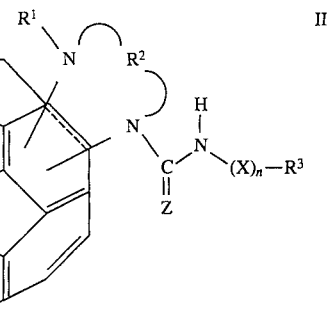

where
$R^1$ is $(C_1-C_4)$-alkyl,
$R^2$ is $(C_2-C_4)$-alkylene or 1,2-cyclo-$(C_3-C_7)$-alkylene,
n is an integer zero or 1,
Z is O or S,
X is $(C_1-C_{12})$-alkylene, $(C_3-C_{12})$-alkenylene or $(C_6-C_{10})$-arylene, where alkylene and alkenylene is unsubstituted or substituted by $(C_1-C_4)$-alkoxy, $(C_1-C_4)$-alkylthio, Cl, Br, I, $(C_1-C_4)$-alkoxycarbonyl, $(C_6-C_{10})$-aryl and/or $(C_6-C_{10})$-aryl-$(C_1-C_4)$-alkyl, where aryl is unsubstituted or is monosubstituted or polysubstituted independently of one another by halogen, $(C_1-C_4)$-alkyl, $(C_1-C_4)$-alkoxy, $CF_3$, CN or $NO_2$, and where arylene is unsubstituted or monosubstituted or polysubstituted independently of one another by halogen, $(C_1-C_4)$-alkyl, $(C_1-C_4)$-alkoxy, $(C_1-C_4)$-alkylthio, $CF_3$, $OCF_3$, CN, $NO_2$ and/or $(C_1-C_4)$-alkoxycarbonyl, $R^3$ is, if n is zero, $(C_1-C_{12})$-alkyl, $(C_3-C_{11})$-alkenyl, $(C_3-C_8)$-alkynyl, $(C_1-C_8)$-perfluoroalkyl, $(C_6-C_{14})$-aryl or trimethylsilyl, where alkyl, alkenyl and alkynyl are unsubstituted or monosubstituted or polysubstituted independently of one another by $(C_1-C_4)$-alkoxy, $(C_1-C_4)$-alkylthio, phenyloxy, phenylthio, halogen, $ClSO_2$ and/or $(C_1-C_4)$-alkoxycarbonyl, and aryl is unsubstituted or monosubstituted or polysubstituted independently of one another by halogen, $(C_1-C_4)$-alkyl which is unsubstituted or substituted by halogen, $(C_1-C_4)$-alkoxy, $NO_2$, CN, $OCF_3$, $ClSO_2$, $SO_3H$, $(C_1-C_4)$-alkanoyloxy, $(C_1-C_4)$-alkoxycarbonyl and/or $(C_1-C_2)$-alkylenedioxy, $R^3$ is, if n=1, hydrogen, $CH_3$ which is unsubstituted or substituted by halogen, $CH=CH_2$, $(C_1-C_4)$-alkoxy, $(C_1-C_4)$-alkylthio, halogen, $(C_6-C_{14})$-aryl, $(C_6-C_{14})$-aryloxy, $(C_6-C_{14})$-aryl-$(C_1-C_4)$-alkyloxy, trimethylsilyloxy, C(O) NHR', C(O) $NR'_2$, COOR', where R' is $(C_1-C_4)$-alkyl, $(C_1-C_6)$-alkanoyloxy, $SO_2R^5$, $OSO_2R^5$, where $R^5$ is $(C_1-C_4)$-alkyl, $(C_6-C_{10})$-aryl or $(C_1-C_4)$-alkyl-$(C_6-C_{10})$-aryl, or $-N=C'Z$ where Z is as defined above, and aryl is unsubstituted or monosubstituted or polysubstituted independently of one another by halogen, $(C_1-C_4)$-alkoxy, $(C_1-C_4)$-alkylthio, $(C_1-C_4)$-alkyl which is unsubstituted or substituted by halogen, $NO_2$, CN, $ClSO_2$, $SO_3H$, $(C_1-C_4)$-alkanoyloxy, $(C_1-C_4)$-alkoxycarbonyl or $(C_6-C_{10})$-aryloxy.

Preferred compounds of the formulae I and II are those in which
Z is O,
X is $(C_1-C_8)$-alkylene, unsubstituted or substituted by $(C_1-C_4)$-alkoxy, $(C_1-C_4)$-alkylthio, $(C_1-C_4)$-alkoxcarbonyl or Cl, or o-, m- or p-phenylene, unsubstituted or substituted by halogen, ($C_1$–$C_4$)-alkoxy, ($C_1$–$C_4$)-alkyl or $CF_3$ and $R^3$ is, if n is zero, ($C_1$–$C_{12}$)-alkyl, allyl, phenyl, benzyl or naphthyl, where alkyl is unsubstituted or monosubstituted or disubstituted independently of one another by ($C_1$–$C_4$)-alkoxy, ($C_1$–$C_4$)-alkylthio, phenyloxy, phenylthio, Cl, Br or ($C_1$–$C_4$)-alkyloxycarbonyl, and phenyl, benzyl or naphthyl is unsubstituted or monosubstituted or polysubstituted independently of one another by halogen, ($C_1$–$C_4$)-alkoxy, ($C_1$–$C_4$)-alkyl, $CF_3$, $NO_2$, CN, ($C_1$–$C_4$)-alkanoyloxy, $ClSO_2$, $SO_3H$ and/or ($C_1$–$C_4$)-alkoxycarbonyl or monosubstituted by methylenedioxy, and $R^3$ is, if n=1, hydrogen, $CH_3$, $ClCH_2$, $BrCH_2$, vinyl, ($C_1$–$C_4$)-alkoxy, ($C_1$–$C_4$)-alkylthio, Cl, Br, phenoxy, benzyloxy, phenyl, naphthyl, C(O)NHR', C(O)NR'$_2$ or COOR', where R' is ($C_1$–$C_4$)-alkyl and where phenyl or naphthyl is unsubstituted or monosubstituted or polysubstituted independently of one another by ($C_1$–$C_4$)-alkoxy, ($C_1$–$C_4$)-alkyl, $CF_3$, $NO_2$, CN, $ClSO_2$, $SO_3H$ and/or ($C_1$–$C_4$)-alkoxycarbonyl, and $R^1$, $R^2$ and n are as defined above.

Particular preference is given to compounds of the formulae I and II in which $R^1$ is $CH_3$ or $C_2H_5$, $R^2$ is ($C_2$–$C_3$)-alkylene or 1,2-cyclo-($C_5$–$C_6$)-alkylene, n is an integer zero or 1, Z is O, X is ($C_1$–$C_7$)-alkylene, unsubstituted or substituted by $CH_3O$, $CH_3S$, $COOCH_3$ or $COOC_2H_5$, or o-, m- or p-phenylene, $R^3$ is, if n is zero, ($C_1$–$C_8$)-alkyl, allyl, phenyl, benzyl or naphthyl, where alkyl is unsubstituted or monosubstituted or disubstituted independently of one another by $CH_3O$, $CH_3S$, $COOCH_3$ or $COOC_2H_5$, and phenyl, benzyl or naphthyl is unsubstituted or monosubstituted or disubstituted independently of one another by F, Cl, Br, $CH_3O$, $C_2H_5O$, $CH_3$, $C_2H_5$, $NO_2$, $ClSO_2$, $SO_3H$, $CF_3$, $COOCH_3$ and/or $COOC_2H_5$ or 1,2-O—$CH_2$—O, and $R^3$ is, if n=1, hydrogen, $CH_3$, $CH_3O$, $CH_3S$, Cl, Br, $C_6H_5O$, $C_6H_5CH_2O$, phenyl, $COOCH_3$, $COOC_2H_5$, C(O) NHR', C(O) N—R'$_2$, where R' is ($C_1$–$C_4$)-alkyl, and phenyl is unsubstituted or substituted by $CH_3O$, $C_2H_5O$, $CH_3$, $CF_3$, $NO_2$, $ClSO_2$, $COOCH_3$ or $COOC_2H_5$.

Very particular preference is given to compounds of the formula I where $R^1$, $R^2$, n, Z, X and $R^3$ are as defined above.

Hydrocarbon radicals such as alkyl, alkylene, alkenyl, alkenylene, alkynyl or else alkoxy may be branched or unbranched. Aryl is, for example, phenyl or naphthyl. Arylalkyl is, for example, benzyl. Arylene is, for example, phenylene. Aryl may be monosubstituted or polysubstituted, preferably monosubstituted, disubstituted, trisubstituted or tetrasubstituted, particularly preferably monosubstituted or disubstituted. In this context, a substituted aryl radical also includes, for example, a substituted aryloxy radical. Perfluoroalkyl is a completely fluorinated alkyl radical. Halogen is fluorine, chlorine, bromine or iodine. ($C_1$–$C_2$)-alkylenedioxy as substituent of phenyl is a 1,2—O— ($CH_2$)$_m$—O radical, where m is 1 or 2.

The invention further provides a process for preparing the fullerene compounds of the formulae I and/or II,

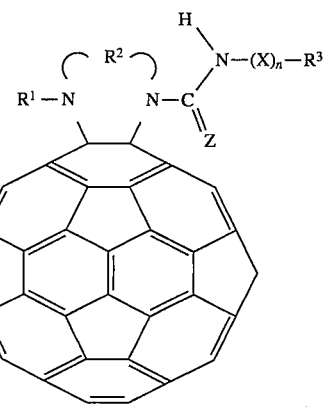

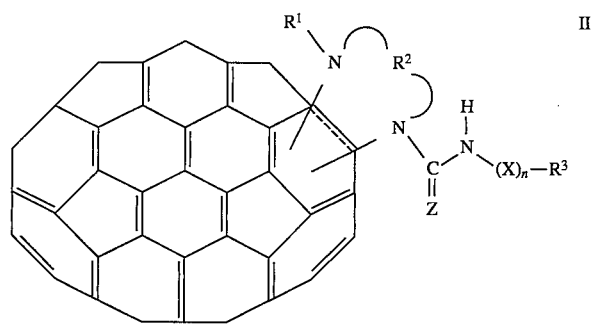

where $R^1$, $R^2$, n, Z, X and $R^3$ are as defined above, which comprises reacting compounds of the formulae III and/or

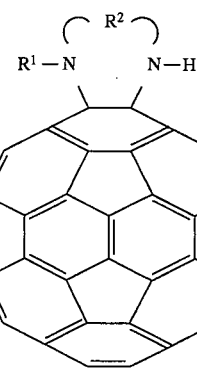

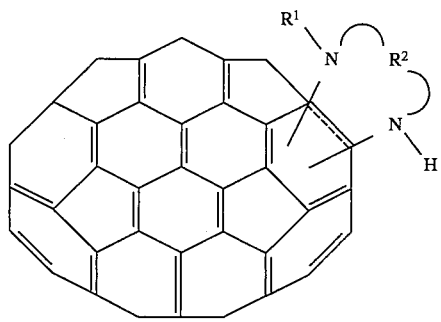

where $R^1$ and $R^2$ are as defined above, with an isocyanate or isothiocyanate of the formula V

where Z, n, X and $R^3$ are as defined above, to give compounds of the formula I and/or II.

Particular preference is given to the preparation of compounds of the formula I from compounds of the formulae III and V.

The reaction of the invention is preferably carried out in a solvent or suspension medium, preferably aromatic, which is inert with respect to the compounds of the formulae I, II, III, IV and V, or a mixture of such solvents or suspension media.

Suitable solvents or suspension media are, for example: toluene, benzene, xylenes, anisole, chlorobenzene, dichlorobenzenes, methylnaphthalenes, chloronaphthalenes, bromobenzene, tetralin, dimethylnaphthalenes, methylthiophenes, and/or tetrachloroethane.

The reaction of the invention can be carried out at a temperature of from −30° C. to 300° C., preferably from +30° C. to 115° C. The reaction can be carried out either in solution or in suspension, i.e. the starting materials, the reactants, and also the compounds of the invention of the formula I and/or II can be present in the reaction mixture in dissolved or undissolved form. The reaction can, however, also take place at a temperature below −30° C. or above +300° C.

The molar ratio of the fullerene derivatives of the formula III and/or IV to the isocyanates or isothiocyanates of the formula V can, in the process of the invention, be from 1:1 to 1:1000, preferably from 1:3 to 1:200, particularly preferably from 1:6 to 1:30, or even smaller than 1:1000.

The reaction of the fullerene derivatives of the formulae III and/or IV with the isocyanates of the formula V (Z=O) proceeds surprisingly quickly and selectively to form the compounds of the formula I or II, even in heterogeneous systems.

The reaction of compounds of the formula III and/or IV with isothiocyanates of the formula V, where Z=S, proceeds at a lower reaction rate compared with the reaction with the isocyanates of the formula V, where Z=O.

The molar ratio of the isocyanates or isothiocyanates of the formula V to the fullerene derivatives of the formula III and/or IV, the reaction temperature and the reaction rate in the process of the invention have the known relationship:

a) the greater the molar ratio, the lower can the reaction temperature be maintained or selected, and b) the greater the molar ratio and the higher the reaction temperature, the greater the reaction rate, which allows shorter reaction times. This last aspect is of particular importance in the reaction of the less reactive isothiocyanates of the formula V (Z=S).

The reaction times can, depending on the abovedescribed parameters, vary within a wide range; they are generally between 10 minutes and 5 days depending on whether isocyanates of the formula V (Z=O) or isothiocyanates of the formula V (Z=S) are being reacted. However, shorter or longer reaction times may be sufficient or necessary.

The aminoureidofullerene or aminothioureidofullerene derivatives of the invention having the formulae I and II are satisfactorily characterized by their chemical properties, chemical composition and their spectroscopic data.

Under chemical properties, the behaviour on chromatography, such as conventional thin-layer and column chromatography and also HPLC serve to characterize the new compounds formed.

The chemical composition of the fullerene derivatives of the invention having the formulae I and II is determined by elemental analyses.

Furthermore, the spectroscopic data of the new compounds of the invention are particularly useful for their unambiguous characterization. These data include the absorption spectra in the UV, visible and IR regions. The fullerene derivatives of the invention show characteristic IR spectra having a sharp band structure. Likewise, the compounds of the invention each have characteristic UV absorptions, i.e. are distinguished by the position of their maxima.

The mass spectra recorded by the FAB (fast atom bombardment) MS method likewise characterize the respective compounds and confirm the molecular weights by the molecular peak, if present and recognizable.

The NMR spectra too, measured both as solid state spectra and, in particular, as solution spectra, are used for the characterization and structure assignment of the compounds of the invention.

For the purpose of isolation and purification, the fullerene derivatives of the invention having the formula I and/or II can be partially precipitated as crystalline materials by concentration of the reaction solution and as such be isolated in a customary manner, e.g. by filtration.

A preferred embodiment for isolation and purification of the compounds of the invention having the formula I and/or II comprises separating the reaction mixture either directly or after prior filtration by column chromatography, preferably on silica gel, into any by-products formed from the compounds of the formula V, unreacted fullerene derivative of the formula III and/or IV and the aminoureidofullerenes or aminothioureido-fullerenes of the formula I and/or II which are formed. The column chromatography on silica gel is advantageously carried out using toluene and dichloromethane and toluene/methanol or dichloromethane/methanol mixtures as eluant.

In thin-layer chromatography (TLC) on silica gel, the compounds of the invention having the formula I mostly run more slowly in the eluants $CH_2Cl_2/C_2H_5OH$ (volume ratio: 100/4) and toluene/methanol (volume ratio: 100/3), i.e. have lower $R_F$ values, than do the starting fullerene derivatives of the formula III. In purification by column chromatography on silica gel 60 (particle size: 0.040–0.063 mm) too, unreacted starting fullerene derivatives of the formula III, if still present, generally run ahead of the fullerene derivatives of the invention having the formula I.

Such chromatographic separations can, on the other hand, also be carried out by the "reversed phase (RP)" method using an appropriate silica gel or using other adsorbents as stationary phase, e.g. $Al_2O_3$. After evaporation of the eluant, the addition compounds of the invention are obtained as solid, frequently crystalline materials. If required, any by-products still present which have been formed from the isocyanates or isothiocyanates of the formula V which were used, for example by action of moisture, can be removed in this state by digestion with aprotic polar solvents such as, for example, ether, tetrahydrofuran, acetonitrile and/or acetone. The fullerene derivatives of the invention having the formula I and/or II which are formed are generally sparingly soluble or quasi-insoluble in such solvents.

It is also a feature of this invention that it provides a simple formation route to the aminoureidofullerene or aminothioureidofullerene derivatives of the formulae I and II and that the reaction products of the formula I and/or II, in particular the compounds of the formula I, can be isolated in pure form in a simple and inexpensive way by conventional column chromatography, i.e. without use of high-pressure liquid chromatography which is complicated in terms of apparatus and suitable only for the preparation of small amounts. The compounds of the invention obtained by column chromatography or by other workup methods can, if necessary, be further purified by recrystallization.

Although for the purposes of the present invention the use of the HPLC method is surprisingly not required for the separation, isolation and purification of the compounds of the invention, the HPLC method is suitable for the characterization of the addition compounds obtained according to the invention. Retention time coupled with the stationary phase used and the liquid phase, the flow velocity and the customary column parameters are reliable material parameters for characterizing pure substances or even mixtures of the invention.

A further advantage of the workup of the reaction mixture by column chromatography, which is possible according to the invention, is that any unreacted starting fullerene derivatives can be simply and cleanly separated off and thus be recovered for reuse. Considering the high price of fullerene compounds, this is of considerable importance.

The fullerene derivatives of the formula III and/or IV, which are required as starting materials, can be prepared by the processes described in German Patent Application P 43 12 632.4 and by Kampe et al. [Angew. Chem. Int. Ed. (Engl.) 32, 1174 (1993)]. The isocyanates and isothiocyanates of the formula V required for the reaction are known or can be prepared by known methods.

The fullerene derivatives of the invention are suitable for use as complexing ligands. This property enables them to be used for modifying catalysts.

Furthermore, the compounds of the invention can be used as such or in modified form for inhibition of enzymes, for example for the inhibition of HIV (human immuno-deficiency virus) enzymes, such as HIV-1 protease, whereby they represent potential biological active substances which can be used, for example, as antiviral agents.

The following examples illustrate the invention without limiting it to the conditions specified by way of example.

If not otherwise indicated in the following examples, column chromatography was carried out on silica gel 60, particle size from 0.040 to 0.063 mm, from E. Merck, Darmstadt and thin-layer chromatography (TLC) was carried out on silica gel 60 $F_{254}$ (layer thickness: 0.25 mm) from Riedel-de Haen AG, Seelze.

EXAMPLE 1

A solution of 180 mg (0.227 mmol) of a fullerene compound of the formula III in which $R^1$ is $CH_3$ and $R^2$ is —$CH_2CH_2$— in 450 ml of toluene was admixed with 0.25 ml (242 mg; 4.24 mmol) of methyl isocyanate and stirred for 2.1 days at 37°–40° C. and for 2.7 days at RT. The clear reaction solution was then evaporated in vacuo at 40° C. to about 40% of the original volume and this solution was allowed to be absorbed on a silica gel 60/toluene column (H: 42 cm; ⌀2.0 cm). After solution with 50 ml of toluene, during which traces of $C_{60}$ (violet color) ran from the column, solution was carried out using $CH_2Cl_2$ (200 ml), $CH_2Cl_2/CH_3OH$ (100:1) (600 ml); (100:2) (300 ml). This gave, after evaporation of the eluant, 140 mg of eluate residue which was dissolved in toluene and filtered through Clarcel (filter aid). After evaporation in vacuo, the residue remaining was suspended in ether, filtered with suction, washed with ether and dried for 8 hours at 80° C., 6–8 mbar. This gave 124 mg (=64.3% yield) of a compound of the formula I in which $R^1$ and $R^3$ are $CH_3$; $R^2$ is —$CH_2CH_2$—; n=zero and Z is O.

$C_{65}H_{11}N_3O$ (849.83) calculated: C 91.87 H 1.30 N 4.94% found: C 88.9 H 1.4 N 4.5%

IR spectrum (powder on KBr): $v_{c=o}$ 1703 cm$^{-1}$ (strongest IR band) The mass spectrum (FAB) shows a molecular mass M=849 (strong M$^\ominus$ peak at m/e 849) Thin-layer chromatography: eluant $CH_2Cl_2/C_2H_5OH$: 100/4 $R_f$: from 0.25 to 0.30.

EXAMPLE 1a

The same reaction as described above was carried out in 500 ml of benzene in place of toluene, with the reaction time being 3.5 days at 38°–41° C. and 3.1 days at RT. After the same workup as described above, 102 mg (52.9% yield) of this fullerene compound of the formula I were obtained after drying.

EXAMPLE 2

A suspension of 100 mg (0,124 mmol) of a fullerene compound of the formula III in which $R^1$ is $C_2H_5$ and $R^2$ is —$CH_2CH_2$— in 100 ml of toluene was admixed at 70° C. with a solution of 357 mg (2.3 mmol) of octyl isocyanate in 5 ml of toluene and stirred for 0.82 days at 70°–72° C. and for 1 day (24 hours) at RT. The reaction solution was then evaporated in vacuo. The residue was suspended in ether and filtered with suction. The filter residue (103 mg of solid) was dissolved in 20 ml of toluene. This solution was allowed to be absorbed on a silica gel 60/toluene column (H: 45 cm; ⌀2.4 cm). Chromatography was carried out under 0.35 bar gauge pressure of nitrogen. After elution with 500 ml of each of toluene, toluene/methanol (100:0.1) and (100:0.2), further elution with 700 ml of toluene/methanol (100:0.2) gave 77 mg of eluate residue after evaporation. This was suspended in ether, filtered with suction and dried for 8 hours at 80° C., 4–6 mbar. This gave 68 mg (=57% yield) of a compound of the formula I in which $R^1$ is $C_2H_5$; $R^2$ is —$CH_2CH_2$—; n=zero; Z is O and $R^3$ is n-$C_8H_{17}$.

$C_{73}H_{27}N_3O$ (962.04) calculated: C 91.14 H 2.83 N 4.37% found: C 89.9 H 3.3 N 4.3% The mass spectrum (FAB) shows a molecular mass M=961 (strong M$^\ominus$ peak at m/e 961) TLC: eluant toluene/methanol: 100/3; $R_f$: 0.45–0.49.

EXAMPLE 3

A suspension of 317 mg (0.4 mmol) of a fullerene compound of the formula III in which $R^1$ is $CH_3$ and $R^2$ is —$CH_2CH_2$— in 250 ml of toluene was admixed at 70° C. with a solution of 1.0 g (8.4 mmol) of phenyl isocyanate in 10 ml of toluene and stirred for 4.7 hours at 70° C. The reaction solution was then evaporated in vacuo, the residue remaining was suspended in ether, the solid was filtered off with suction, washed with ether and dried in vacuo. This gave 428 mg of solid which was dissolved in 50 ml of toluene and absorbed on a silica gel 60/toluene column (H: 44 cm; ⌀: 2.0 cm). Elution was carried out at 0.35 bar gauge pressure of $N_2$ using 200 ml of toluene; 500 ml of $CH_2Cl_2$; 500 ml of $CH_2Cl_2/CH_3OH$ (100:1) and 200 ml of $CH_2Cl_2/CH_3OH$ (100:1.5). Further elution with 300 ml of $CH_2Cl_2/CH_3OH$ (100:1.5) and 700 ml of $CH_2Cl_2/CH_3OH$ (100:2) gave, after evaporation of the eluant, 365 mg of eluate residue which was suspended in ether and filtered with suction. After drying (8 hours, 80° C., 5–7 mbar) this gave 351 mg (96.2% yield) of a compound of the formula I in which $R^1$ is $CH_3$; $R^2$ is —$CH_2CH_2$—; n=zero; Z is O and $R^3$ is $C_6H_5$.

$C_{70}H_{13}N_3O$ (911.90) calculated: C 92.20 H 1.44 N 4.61% found: C 90.1 H 1.5 N 4.2%

The mass spectrum (FAB) shows a molecular mass M=911 (strong M$^\ominus$ peak at m/e 911) TLC: toluene/methanol: 10/1: $R_F$: 0.39–0.42 IR spectrum: $v_{c=o}$ 1706; $v_{NH,C-N}$ 1414 cm$^{-1}$

EXAMPLE 4

A suspension of 160 mg (0.2 mmol) of a compound of the formula III in which $R^1$ is $CH_3$ and $R^2$ is —$CH_2CH_2$— in 150 ml of toluene was admixed at 70° C. with a solution of 600 mg (4.44 mmol) of phenyl isothiocyanate in 8 ml of toluene and stirred for 10.1 days at 65°–68° C. and for 5.9 days at RT. The mixture was then evaporated in vacuo, the residue remaining was suspended in ether, the solid was filtered off with suction and dissolved in 75 ml of $CS_2$. This solution was absorbed on a silica gel 60/toluene column (H: 40 cm; ⌀: 2.2 cm). Elution was carried out at 0.35 bar gauge pressure of $N_2$ using 500 ml of toluene and toluene/methanol (500 ml; 100:0.1 and 1 l, 100:0.2). Further elution with 500 ml of toluene/methanol (100:0.2) gave, after evaporation of the eluant, 116 mg of eluate residue (TLC uniform) which was suspended in ether and filtered with suction. After drying (cf. Example 3), this gave 106 mg (57.1% yield) of TLC-pure compound of the formula I in which $R^1$ is $CH_3$; $R^2$ is —$CH_2CH_2$—; n=zero; Z is S and $R^3$ is $C_6H_5$.

$C_{70}H_{13}N_3S$ (927.96) calculated: C 90.60 H 1.41 N 4.53 S 3.46% found: C 88.1 H 1.4 N 4.3 S 3.4% The mass spectrum (FAB) shows a molecular mass M=927 (strong $M^{\ominus}$ peak at m/e 927) IR spectrum (powder on KBr): $v_{C=S}$ 1424; $v_{C-N}$ 1300 cm$^{-1}$ Thin-layer chromatography: eluant: toluene/methanol 100/3; $R_F$ 0.59–0.60

EXAMPLE 5

In a manner similar to that described in Example 3, a suspension of 200 mg (0.252 mmol) of the same compound of the formula III as in Example 3 and 1.0 g (5.34 mmol) of 3-trifluoromethylphenyl isocyanate in 205 ml of toluene was stirred for 3.6 hours at 70° C. and subsequently worked up and chromatographed on silica gel 60 (H: 28 cm; ⌀: 2.0 cm). After elution with 200 ml of toluene, 200 ml of $CH_2Cl_2$ and 400 ml of $CH_2Cl_2/CH_3OH$ (100/1), elution with 300 ml of $CH_2Cl_2/CH_3OH$ (100/1) gave, after evaporation, 219 mg of eluate residue from which there were obtained, these were obtained, after similar treatment to that described in Example 3, 202 mg (81.8% yield) of TLC-pure compound of the formula I in which $R^1$ is $CH_3$; $R^2$ is —$CH_2CH_2$—; n=zero; Z is O and $R^3$ is 3-trifluoromethylphenyl.

$C_{71}H_{12}F_3N_3O$ (979.90) calculated: C 87.03 H 1.23 F 5.82 N 4.29% found: C 85.4 H 1.6 F 4.9 N 3.8%

According to the mass spectrum (FAB), molecular mass M=979 (strong $M^{\ominus}$ peak at m/e 979) IR spectrum: $v_{C=O}$ 1707 cm$^{-1}$ TLC (toluene/methanol 10/1): $R_F$ 0.52–0.54

EXAMPLE 6

In a similar manner to that described in Example 3 and Example 5, 323 mg (0.4 mmol) of compound of the formula III ($R^1$:$C_2H_5$;$R^2$:—$CH_2CH_2$—) and 1.37 g (8.4 mmol) of 3,4-methylenedioxyphenyl isocyanate and 260 ml of toluene gave, after stirring for 4.7 hours at 72° C., workup and chromatography on silica gel 60 (H: 45 cm; ⌀: 2.0 cm) (elution: 500 ml of toluene, 500 ml of $CH_2Cl_2$, 250 ml of each of $CH_2Cl_2/CH_3OH$ (100:0.2); (100:0.5); (100:0.75) and (100:1); then 500 ml of $CH_2Cl_2/CH_3OH$ (100:1)), 255 mg (65.7% yield) of TLC-pure compound of the formula I in which $R^1$ is $C_2H_5$; $R^2$ is —$CH_2CH_2$—; n=zero; Z is O and $R^3$ is 3,4-methylenedioxyphenyl

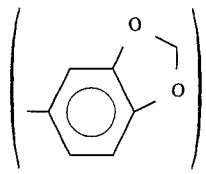

$C_{72}H_{15}N_3O_3$ (969.94) calculated: C 89.16 H 1.56 N 4.33% found: C 86.3 H 2.0 N 4.5%

According to the mass spectrum (FAB), molecular mass M=969 (strong $M^{\ominus}$ peak at m/e 969) IR spectrum: $v_{C=O}$ 1705 cm$^{-1}$ TLC (toluene/methanol: 100/3) $R_F$ 0.29–0.30

EXAMPLE 7

In a similar manner to that described in Example 3, a suspension of 150 mg (0.19 mmol) of the same compound of the formula III as in Example 3 and 745 mg (3.42 mmol) of 4-chlorosulfonylphenyl isocyanate in 158 ml of toluene was stirred for 6.25 hours at 70° C. The reaction mixture was then filtered with suction, the filter residue was washed with toluene and ether and the filtrate was evaporated in vacuo. The filtrate residue was suspended in 20 ml of $CS_2$, the solid was filtered off with suction and washed with $CS_2$ and ether and the filtrate was again evaporated in vacuo. The residue then remaining was suspended in 50 ml of ether and filtered with suction, giving 108 mg of crude product of the formula I. This was, dissolved in 20 ml of toluene, chromatographed on silica gel 60 (H: 38 cm; ⌀: 2.4 cm) at 0,35 bar gauge pressure of $N_2$. After elution with 200 ml of each of toluene; toluene/methanol (100:0.3); (100:0.6) and (100:1), 800 ml of toluene/methanol (100:1) gave, after evaporation, 107 mg of eluate residue which was further treated as described in Example 3. This gave 94 mg (49.0% yield) of TLC-pure compound of the formula I in which $R^1$ is $CH_3$; $R^2$ is —$CH_2CH_2$—; n=zero; Z is O and $R^3$ is 4-hydroxysulfonylphenyl

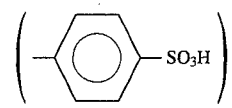

$C_{70}H_{13}N_3O_4S$ (991.96) calculated: C 84.76 H 1.32 N 4.24 S 3.23% found: C 81.1 H 1.6 N 4.2 S 3.5%

According to the mass spectrum (FAB), molecular mass M=991 (strong $M^{\ominus}$ peak at m/e 990) IR spectrum (powder on KBr) $v_{C=O}$ 1720; $v_{NH, C-N}$ 1412; $v_{S=O}$ 1178 cm$^{-1}$ TLC (toluene/methanol: 100/3) $R_F$ 0.23–0.25

EXAMPLE 8

A suspension of 532 mg (0.67 mmol) of a compound of the formula III in which $R^1$ is $CH_3$ and $R^2$ is $(CH_2)_2$ in 400 ml of toluene was admixed at 68° C. with a solution of 1.64 g (12.7 mmol) of ethyl 2-isocyanatoacetate in 8 ml of toluene and was stirred for 2 days at 68°–71° C. and for 4.9 days at RT. The slightly turbid reaction solution was filtered through Clarcel, evaporated to about 100 ml in vacuo and then absorbed on a silica gel 60/toluene column (H: 42 cm; ⌀: 2.0 cm). After elution (0.35 bar gauge pressure of $N_2$) with 500 ml of toluene, 1 l of each of toluene/methanol (100:0.5), (100:1) and (100:2) gave, after evaporation in vacuo, 665 mg of eluate residue. This was dissolved in toluene, the solution was filtered through Clarcel, evaporated in vacuo, the residue remaining was suspended in ether, filtered with suction and washed with ether. After drying (80° C., 4 hours, 5–7 mbar), this gave 588 mg (95.2% yield) of TLC-pure compound of the formula I in which $R^1$ is $CH_3$; $R^2$ is $(CH_2)_2$; n=1; Z is O; X is $CH_2$ and $R^3$ is $COOC_2H_5$. $C_{68}H_{15}N_3O_3$ (921.89) calculated: C 88.59 H 1.64 N 4.56% found: C 87.8 H 2.1 N 4.3% Mass spectrum (FAB): Molecular mass M=921 (strong $M^{\ominus}$ peak at m/e 921) IR spectrum $v_{C=O}$ 1712; 1745; $v_{C-O}$ 1200; vNH, C—N 1432 cm$^{-1}$ TLC (toluene/methanol 100:1): $R_F$ 0.09–0.13

EXAMPLE 9

A solution of 540 mg (0.68 mmol) of a compound of the formula III in which $R^1$ is $CH_3$ and $R^2$ is $(CH_2)_2$ in 1300 ml of toluene was admixed at 65° C. with a solution of 2.04 g (15.8 mmol) of methyl 3-isocyanatopropionate in 10 ml of toluene and was stirred for 2.25 days at 65° C. and for 2.7 days at RT. The reaction solution was then evaporated in vacuo to about 160 ml, this solution was allowed to be absorbed on a silica gel 60/toluene column (H: 50 cm; ø: 2.5 cm) and successively eluted at 0.35 bar gauge pressure of $N_2$ with 500 ml each of toluene, $CH_2Cl_2$ and $CH_2Cl_2/CH_3OH$ (100:0.5). A dark zone was subsequently eluted with 500 ml of $CH_2Cl_2/CH_3OH$ (100:1), which gave, after evaporation, 500 mg of eluate residue. This was, dissolved in toluene, filtered through Clarcel. The filtrate was evaporated in vacuo, the residue was suspended in n-heptane and filtered with suction and dried for 6 hours at 50° C., 4–6 mbar. This gave 456 mg (=72.7% yield) of TLC-pure compound of the formula I in which $R^1$ is $CH_3$; $R^2$ is $(CH_2)_2$; n=1, Z is O; X is $(CH_2)_2$ and $R^3$ is $COOCH_3$.

$C_{68}H_{15}N_3O_3$ (921.89) calculated: C 88.59 H 1.64 N 4.56% found: C 86.3 H 2.0 N 4.2% Mass spectrum (FAB): Molecular mass M=921 (strong M$^\ominus$ peak at m/e 921. MH$^\oplus$ peak at m/e 922) IR spectrum $v_{N-H}$ 3350; $v_{C-O}$ 1704; 1733; $v_{C-O}$ 1200; $v_{NH, C-N}$ 1445 cm$^{-1}$ TLC ($CH_2Cl_2$/$CH_3OH$: 100/4) $R_F$ 0.30–0.32

EXAMPLE 10

In a manner similar to Example 8, a suspension of 586 mg (0.74 mmol) of a compound of the formula III ($R^1$:$CH_3$; $R^2$: $(CH_2)_2$) and 1.81 g (12.64 mmol) of ethyl 3-isocyanatopropionate in 508 ml of toluene was stirred for 2.6 days at 70° C. and for 2.2 days at RT. The mixture was subsequently worked up and chromatographed (column: H 53 cm; ø2.5 cm) as described in Example 9. After elution with 500 ml of each of toluene; $CH_2Cl_2$ and $CH_2Cl_2/CH_3OH$ (100:0.3), further elution with 500 ml of each of $CH_2Cl_2/CH_3OH$ (100:0.5) and (100:1) gave, after evaporation, 535 mg of eluate residue which was treated as described in Example 9, giving 485 mg (70% yield) of TLC-pure compound of the formula I in which $R^1$ is $CH_3$; $R^2$ is $(CH_2)_2$; n=1; Z is O; X is $(CH_2)_2$ and $R^3$ is $COOC_2H_5$.

$C_{69}H_{17}N_3O_3$ (935.92) calculated: C 88.55 H 1.83 N 4.49% found: C 86.6 H 2.2 N 4.0% Mass spectrum (FAB): Molecular mass M=935 (strong M$^\ominus$ peak at m/e 935). TLC (toluene/methanol: 100/3): $R_F$ 0.27–0.28

EXAMPLE 11

In a manner similar to that in Example 8, a suspension of 300 mg (0.37 mmol) of a compound of the formula III ($R^1$:$C_2H_5$; $R^2$: $(CH_2)_2$) and 978 mg (7.57 mmol) of ethyl 2-isocyanatoacetate in 245 ml of toluene was stirred for 6.9 days at 70°–72° C. and for 7.9 days at RT. The reaction solution was subsequently absorbed on a silica gel 60/toluene column (H: 42 cm; ø: 2.5 cm). After elution at 0.35 bar gauge pressure of $N_2$ with 500 ml of each of $CH_2Cl_2$ and $CH_2Cl_2/CH_3OH$ (100:0.2) and 1 l of $CH_2Cl_2/CH_3OH$ (100:0.5), use of 1000 ml (100:0.5) and 200 ml (100:0.8) gave, after evaporation, 310 mg of eluate residue which was treated as described in Example 9, giving 291 mg (84% yield) of TLC-pure compound of the formula I in which $R^1$ is $C_2H_5$; $R^2$ is $(CH_2)_2$; n=1; Z is O; X is $CH_2$ and $R^3$ is $COOC_2H_5$.

$C_{69}H_{17}N_3O_3$ (935.92) calculated: C 88.55 H 1.83 N 4.49% found: C 85.8 H 2.0 N 4.5% Mass spectrum (FAB): Molecular mass M=935 (strong M$^\ominus$ peak at m/e 935). IR spectrum: vC=O 1712; 1748; vC—O 1205; vNH, C—N 1435 cm−1 TLC (toluene/methanol: 100/3): RF 0.38

EXAMPLE 12

A solution of 363 mg (0.45 mmol) of a compound of the formula III ($R^1$:$C_2H_5$; $R^2$: $(CH_2)_2$) and 1.28 g (9.91 mmol) of methyl 3-isocyanatopropionate in 858 ml of toluene was stirred for 3.2 days at 65° C. and for 2.7 days at RT, and then evaporated in vacuo to about 200 ml. This solution was absorbed on a silica gel 60/toluene column (H: 45 cm; ø: 2.5 cm). Elution was carried out successively at 0.35 bar gauge pressure of $N_2$ with 500 ml of each of toluene and $CH_2Cl_2$. Subsequent elution with 500 ml of each of $CH_2Cl_2/CH_3OH$ (100:0.5) and (100:1) gave, after evaporation, 305 mg of eluate residue. This was, dissolved in toluene, filtered through Clarcel and the filtrate was subsequently evaporated. The residue obtained was suspended in ether, filtered with suction and washed with ether. After drying (8 hours, 60° C., 4–6 mbar), this gave 288 mg (=68.4% yield) of TLC-pure compound of the formula I in which $R^1$ is $C_2H_5$; $R^2$ is $(CH_2)_2$; n=1; Z is O; X is $(CH_2)_2$ and $R^3$ i s $COOCH_3$.

$C_{69}H_{17}N_3O_3$ (935.92) calculated: C 88.55 H 1.83 N 4.49% found: C 88.4 H 2.3 N 4.4% Mass spectrum (FAB): Molecular mass M=935 (strong M$^\ominus$ peak at m/e 935). TLC ($CH_2Cl_2/CH_3OH$: 100/3) $R_F$: 0.39–0.42

EXAMPLE 13

A suspension of 182 mg (0.23 mmol) of a compound of the formula III ($R^1$: $CH_3$; $R^2$: $(CH_2)_2$) and 935 mg (4.6 mmol) of ethyl 2-isocyanato-4-methylthiobutyrate in 188 ml of toluene was stirred for 6.17 hours at 71° C. The solution was subsequently evaporated in vacuo, the residue remaining was suspended in ether, filtered with suction and washed with ether. The solid (203 mg) was dissolved in 50 ml of toluene and absorbed on a silica gel 60/toluene column (H: 44 cm; ø: 2.5 cm). Elution was carried out successively at 0.35 bar gauge pressure of $N_2$ with 200 ml of toluene and 500 ml of each of toluene/methanol (100:0.2), (100:0.3) and (100:0.4). Further elution with 1 l of toluene/methanol (100:0.4) gave, after evaporation, 63 mg of eluate residue which was suspended in ether, filtered with suction and dried for 8 hours at 80° C., 4–7 mbar. This gave 43 mg (18.8% yield) of TLC-pure compound of the formula I in which $R^1$ is $CH_3$; $R^2$ is $(CH_2)_2$; n=1; Z is O; X is

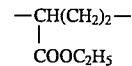

and $R^3$ is $SCH_3$. $C_{71}H_{21}N_3O_3S$ (996.04) calculated: C 85.62 H 2.13 N 4.22 S 3.22% found: C 84.0 H 2.1 N 4.3 S 3.8% Mass spectrum (FAB): Molecular mass M=995 (strong M$^\ominus$ peak at m/e 995) TLC (toluene/methanol: 100/3): $R_F$ 0.32–0.34

EXAMPLE 14

A suspension of 190 mg (0.24 mmol) of a compound of the formula III ($R^1$:$CH_3$; $R^2$: $(CH_2)_2$) and 1.0 g (7.49 mmol) of chloro-tert-butyl isocyanate in 185 ml of toluene was stirred for 1.93 days at 70°–71° C. and subsequently filtered at RT. The filtrate was evaporated in vacuo, the residue remaining was suspended in ether and the solid was filtered off with suction. This (224 mg) was, dissolved in 130 ml of toluene, absorbed on a silica gel 60/toluene column (H: 43 cm; ø: 2.5 cm). Elution was carried out successively at 0.35 bar gauge pressure of $N_2$ with 500 ml of toluene, 500 ml of toluene/methanol (100:0.1) and 800 ml (100:0.2). Further elution with 1 l of toluene/methanol (100:0.2) gave, after evaporation, 155 mg of eluate residue which was suspended in ether, filtered with suction and dried for 8 hours at 80° C., 6–7 mbar. This gave 140 mg (63% yield) of TLC-pure compound of the formula I in which $R^1$ is $CH_3$; $R^2$ is $(CH_2)_2$; n=1; Z is O; X is —$C(CH_3)_2$—$CH_2$— and $R^3$ is Cl.

$C_{68}H_{16}ClN_3O$ (926.34) calculated: C 88.17 H 1.74 Cl 3.83 N 4.54 found: C 87.1 H 1.5 Cl 4.3 N 4.3 Mass spectrum (FAB): Molecular mass M=925; 927 (strong $M^\ominus$ peak at m/e 925) (based on $^{35}$ Cl). IR spectrum: $v_{c=o}$ 1696; $v_{NH,\ C-N}$ 1422 cm$^{-1}$ TLC (toluene/methanol: 100/3): $R_F$ 0.46–0.47

EXAMPLE 15

A suspension of 190 mg (0.235 mmol) of a compound of the formula III ($R^1$:$C_2H_5$; $R^2$: $(CH_2)_2$) and 1.195 g (7.286 mmol) of 2-bromoisopropyl isocyanate in 155 ml of toluene was stirred for 1.9 days at 70° C. and subsequently evaporated in vacuo. The residue was suspended in ether; the solid was filtered off with suction, washed with ether and, dissolved in 150 ml of toluene, absorbed on a silica gel 60/toluene column (H: 43 cm; ø: 2.5 cm). Elution was carried out successively at 0.35 bar gauge pressure of $N_2$ with 500 ml of each of toluene and toluene/methanol (100:0.1). Further elution with 600 ml of toluene/methanol (100:0.1) gave, after evaporation, 65 mg of eluate residue which was suspended in ether, filtered with suction and dried for 8 hours at 80° C., 6–8 mbar. This gave 54 mg (23.7% yield) of TLC-pure compound of the formula I in which $R^1$ is $C_2H_5$; $R^2$ is $(CH_2)_2$; n=1; Z is O; X is —$CH(CH_3)$—$CH_2$— and $R^3$ is Br.

$C_{68}H_{16}BrN_3O$ (970.8) calculated: C 84.13 H 1.66 Br 8.23 N 4.33% found: C 79.3 H 1.7 Br 10.1 N 4.5% Mass spectrum (FAB): Molecular mass M=969; 970; 971; 972 (strong $M^\ominus$ peaks at m/e 969; 970; 971 and 972) (resulting from the isotopes of bromine). TLC (toluene/methanol: 100/3): $R_F$ 0.34–0.36

What is claimed is:
1. A compound of the formula I or II

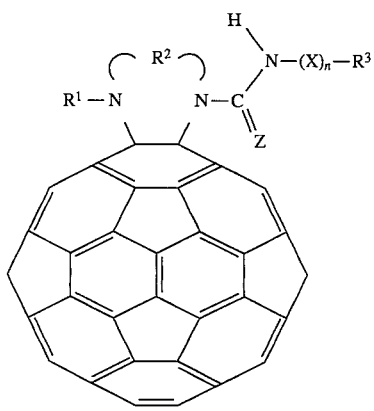

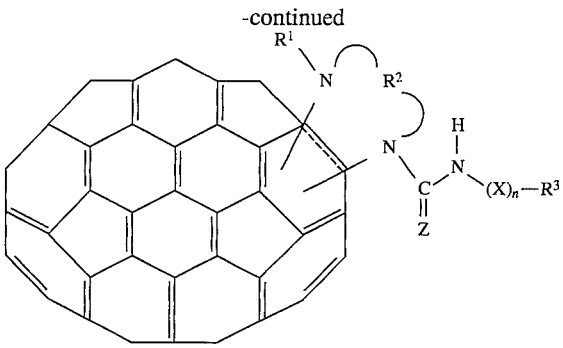

where
$R^1$ is ($C_1$–$C_4$)-alkyl,
$R^2$ is ($C_2$–$C_4$)-alkylene or 1,2-cyclo-($C_3$–$C_7$)-alkylene,
n is an integer zero or 1,
Z is O or S,
X is ($C_1$–$C_{12}$)-alkylene, ($C_3$–$C_{12}$)-alkenylene or ($C_6$–$C_{10}$)arylene, where alkylene and alkenylene is unsubstituted or substituted by ($C_1$–$C_4$)-alkoxy, ($C_1$–$C_4$)-alkylthio, Cl, Br, I, ($C_1$–$C_4$)-alkoxycarbonyl, ($C_6$–$C_{10}$)-aryl and/or ($C_6$–$C_{10}$)-aryl($C_1$–$C_4$)-alkyl, where aryl is unsubstituted or is monosubstituted or polysubstituted independently of one another by halogen, ($C_1$–$C_4$)-alkyl, ($C_1$–$C_4$)-alkoxy, $CF_3$, CN or $NO_2$, and where arylene is unsubstituted or monosubstituted or polysubstituted independently of one another by halogen, ($C_1$–$C_4$)-alkyl, ($C_1$–$C_4$)-alkoxy, ($C_1$–$C_4$)-alkylthio, $CF_3$, $OCF_3$, CN, $NO_2$ and/or ($C_1$–$C_4$)-alkoxycarbonyl,
$R^3$ is, if n is zero, ($C_1$–$C_{12}$)-alkyl, ($C_3$–$C_{11}$)-alkenyl, ($C_3$–$C_8$)-alkynyl, ($C_1$–$C_8$)-perfluoroalkyl, ($C_6$–$C_{14}$)-aryl or trimethylsilyl, where alkyl, alkenyl and alkynyl are unsubstituted or monosubstituted or polysubstituted independently of one another by ($C_1$–$C_4$)-alkoxy, ($C_1$–$C_4$)-alkylthio, phenyloxy, phenylthio, halogen, $ClSO_2$ and/or ($C_1$–$C_4$)-alkoxycarbonyl, and aryl is unsubstituted or monosubstituted or polysubstituted independently of one another by halogen, ($C_1$–$C_4$)-alkyl which is unsubstituted or substituted by halogen, ($C_1$–$C_4$)-alkoxy, $NO_2$, CN, $OCF_3$, $ClSO_2$, $SO_3H$, ($C_1$–$C_4$)-alkanoyloxy, ($C_1$–$C_4$)-alkoxycarbonyl and/or ($C_1$–$C_2$)-alkylenedioxy,
$R^3$ is, if n=1, hydrogen, $CH_3$ which is unsubstituted or substituted by halogen,
$CH=CH_2$, ($C_1$–$C_4$)-alkoxy, ($C_1$–$C_4$)-alkylthio, halogen, ($C_6$–$C_{14}$)-aryl, aryloxy, ($C_6$–$C_4$)-aryl-($C_1$–$C_4$)-alkyloxy, trimethylsilyloxy, C(O)—NHR', C(O)$NR'_2$, COOR', where R' is ($C_1$–$C_4$)-alkyl,
($C_1$–$C_6$)-alkanoyloxy, $SO_2R^5$, $OSO_2R^5$ where $R^5$ is ($C_1$–$C_4$)-alkyl, ($C_6$–$C_{10}$)-aryl or ($C_1$–$C_4$)-alkyl-($C_6$–$C_{10}$)-aryl, or —N=C=Z where Z is as defined above,
and aryl is unsubstituted or monosubstituted or polysubstituted independently of one another by halogen, ($C_1$–$C_4$)-alkoxy, ($C_1$–$C_4$)-alkylthio, ($C_1$–$C_4$)-alkyl which is unsubstituted or substituted by halogen, $NO_2$, CN, $ClSO_2$, $SO_3H$, ($C_1$–$C_4$)-alkanoyloxy, ($C_1$–$C_4$)-alkoxycarbonyl or ($C_6$–$C_{10}$)aryloxy.
2. A compound of formula II as claimed in claim 1.
3. A compound of the formula I or II as claimed in claim 1, wherein
Z is O,
X is ($C_1$–$C_8$)-alkylene, unsubstituted or substituted by ($C_1$–$C_4$)-alkoxy, ($C_1$–$C_4$)-alkylthio, ($C_1$–$C_4$)-alkoxycarbonyl or Cl, or o-, m- or p-phenylene, unsubstituted or substituted by halogen, $(C_1-C_4)$-alkoxy, $(C_1-C_4)$-alkyl or $CF_3$, and $R^3$ is, if n is zero, $(C_1-C_{12})$-alkyl, allyl, phenyl, benzyl or naphthyl, where alkyl is unsubstituted or monosubstituted or disubstituted independently of one another by $(C_1-C_4)$-alkoxy, $(C_1-C_4)$-alkylthio, phenyloxy, phenylthio, Cl, Br or $(C_1-C_4)$-alkyloxycarbonyl, and phenyl, benzyl or naphthyl is unsubstituted or monosubstituted or polysubstituted independently of one another by halogen, $(C_1-C_4)$-alkoxy, $(C_1-C_4)$-alkyl, $CF_3$, $NO_2$, CN, $(C_1-C_4)$-alkanoyloxy, $ClSO_2$, $SO_3H$ and/or $(C_1-C_4)$-alkoxycarbonyl or monosubstituted by methylenedioxy, and $R^3$ is, if n=1, hydrogen, $CH_3$, $ClCH_2$, $BrCH_2$, vinyl, $(C_1-C_4)$-alkoxy, $(C_1-C_4)$-alkylthio, Cl, Br, phenoxy, benzyloxy, phenyl, naphthyl, $C(O)NHR'$, $C(O)NR'_2$ or $COOR'$, where R' is $(C_1-C_4)$-alkyl and where phenyl or naphthyl is unsubstituted or monosubstituted or polysubstituted independently of one another by $(C_1-C_4)$-alkoxy, $(C_1-C_4)$-alkyl, $CF_3$, $NO_2$, CN, $ClSO_2$, $SO_3H$ and/or $(C_1-C_4)$-alkoxycarbonyl, and $R^1$, $R^2$ and n are as defined above.

4. A compound of the formula I and/or II as claimed in claim 1, wherein $R^1$ is $CH_3$ or $C_2H_5$, $R^2$ is $(C_2-C_3)$-alkylene or 1,2-cyclo-$(C_5-C_6)$-alkylene, n is an integer zero or 1, Z is O, X is $(C_1-C_7)$-alkylene, unsubstituted or substituted by $CH_3O$, $CH_3S$, $COOCH_3$ or $COOC_2H_5$, or o-, m- or p-phenylene, $R^3$ is, if n is zero, $(C_1-C_8)$-alkyl, allyl, phenyl, benzyl or naphthyl, where alkyl is unsubstituted or monosubstituted or disubstituted independently of one another by $CH_3O$, $CH_3S$, $COOCH_3$ or $COOC_2H_5$, and phenyl, benzyl or naphthyl is unsubstituted or monosubstituted or disubstituted independently of one another by F, Cl, Br, $CH_3O$, $C_2H_5O$, $CH_3$, $C_2H_5$, $NO_2$, $ClSO_2$, $SO_3H$, $CF_3$, $COOCH_3$ and/or $COOC_2H_5$ or 1,2—O—$CH_2$—O, and $R^3$ is, if n=1, hydrogen, $CH_3$, $CH_3O$, $CH_3S$, Cl, Br, $C_6H_5O$, $C_6H_5CH_2O$, phenyl, $COOCH_3$, $COOC_2H_5$, $C(O)NHR'$, $C(O)N-R'_2$, where R' is $(C_1-C_4)$-alkyl, and phenyl is unsubstituted or substituted by $CH_3O$, $C_2H_5O$, $CH_3$, $CF_3$, $NO_2$, $ClSO_2$, $COOCH_3$ or $COOC_2H_5$.

5. A compound of the formula I as claimed in claim 1.

* * * * *